US011207084B2

(12) United States Patent
Feng et al.

(10) Patent No.: US 11,207,084 B2
(45) Date of Patent: Dec. 28, 2021

(54) TOOL BIT FOR AN ULTRASONIC OSTEOTOME

(71) Applicant: BEIJING SMTP TECHNOLOGY CO., LTD., Beijing (CN)

(72) Inventors: Zhen Feng, Beijing (CN); Qun Cao, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 235 days.

(21) Appl. No.: 16/170,687

(22) Filed: Oct. 25, 2018

(65) Prior Publication Data
US 2019/0059912 A1 Feb. 28, 2019

Related U.S. Application Data

(63) Continuation of application No. PCT/CN2017/080906, filed on Apr. 18, 2017.

(30) Foreign Application Priority Data

Apr. 28, 2016 (CN) .......................... 201610272984.8

(51) Int. Cl.
A61B 17/16 (2006.01)
A61B 17/32 (2006.01)

(52) U.S. Cl.
CPC .......... A61B 17/1659 (2013.01); A61B 17/16 (2013.01); A61B 17/1615 (2013.01);
(Continued)

(58) Field of Classification Search
CPC ............ A61B 17/1659; A61B 17/1615; A61B 17/320068; A61B 2017/320074;
(Continued)

(56) References Cited

U.S. PATENT DOCUMENTS 4,188,952 A  2/1980 Loschilov et al.
5,318,570 A  7/1994 Hood et al.
(Continued)

FOREIGN PATENT DOCUMENTS

CN    1665450 A    9/2005
CN  202086526 U   12/2011
(Continued)

OTHER PUBLICATIONS

International Search Report for PCT Application No. PCT/CN2017/080906; State Intellectual Property Office of P.R. China; Beijing, China; dated Jun. 28, 2017.
(Continued)

Primary Examiner — Kevin T Truong
Assistant Examiner — Tracy L Kamikawa
(74) Attorney, Agent, or Firm — Thomas E. Lees, LLC

(57) ABSTRACT

Disclosed is a tool bit for an ultrasonic osteotome, comprising a cutting portion (1) located at a front end of the tool bit for an ultrasonic osteotome, a connecting portion (2) located at a rear end of the tool bit for an ultrasonic osteotome and connected with the cutting portion (1). The cutting portion (1) has a grinding part (3) for grinding and a blade part (4) for cutting at a front end thereof, and the grinding part (3) and the blade (4) are integrally formed. The tool bit for an ultrasonic osteotome is of an integral structure formed by grinding part (3) and blade (4). During an operation, a medical worker can use the tool bit for an ultrasonic osteotome for multiple uses with no need to replace the tool bit frequently, thus reducing the operation time, greatly improving the efficiency of surgery, reducing the risk of surgery and the sufferings of a patient. At the same time, the integration of two different types of tool bits can also lower production costs and save manpower and material resources. The tool (Continued)

bit for an ultrasonic osteotome of the disclosure can be operated conveniently and comfortably with high safety.

9 Claims, 7 Drawing Sheets

(52) U.S. Cl.
CPC ...... *A61B 17/32* (2013.01); *A61B 17/320068* (2013.01); *A61B 2017/320074* (2017.08)

(58) Field of Classification Search
CPC ....... B23B 37/00; B23B 51/08; B23B 51/009; B24B 1/04; B28D 1/14; B28D 5/02; B28D 5/021
See application file for complete search history.

(56) References Cited

U.S. PATENT DOCUMENTS

| | | | | |
|---|---|---|---|---|
| 5,387,215 | A * | 2/1995 | Fisher | A61B 17/1659 606/79 |
| 7,618,220 | B2 * | 11/2009 | Al-Hussain | B23B 51/08 407/29.13 |
| 8,142,460 | B2 * | 3/2012 | Cotter | A61B 17/1604 606/169 |
| 8,366,713 | B2 * | 2/2013 | Long | A61F 2/30734 606/80 |
| 8,430,897 | B2 * | 4/2013 | Novak | A61B 17/320068 606/169 |
| 2006/0004396 | A1 | 1/2006 | Easley et al. | |
| 2006/0235306 | A1 | 10/2006 | Cotter et al. | |
| 2009/0326535 | A1 | 12/2009 | Blus | |
| 2012/0046682 | A1 | 2/2012 | Nelson et al. | |
| 2013/0304070 | A1 | 11/2013 | Nelson et al. | |
| 2020/0178998 | A1 * | 6/2020 | Behzadi | A61B 17/1666 |

FOREIGN PATENT DOCUMENTS

| | | |
|---|---|---|
| CN | 202920294 U | 5/2013 |
| CN | 103153216 A | 6/2013 |
| CN | 204133550 U | 2/2015 |
| CN | 105326541 A | 2/2016 |
| DE | 29816064 U1 | 11/1998 |
| JP | 2003-126110 A | 5/2003 |
| WO | 2015/010506 A1 | 1/2015 |

OTHER PUBLICATIONS

Written Opinion of the International Searching Authority for PCT Application No. PCT/CN2017/080906; State Intellectual Property Office of the P.R. China; Beijing, China; dated Jun. 28, 2017.

Chinese Office Action for Chinese Patent Application No. 201610272984.8, dated Apr. 2, 2019.

Notification of Transmittal of Translation of the International Preliminary Report on Patentability for PCT Application No. PCT/CN2017/080906; The International Bureau of WIPO; Geneva, Switzerland, dated Nov. 8, 2018.

International Preliminary Report on Patentability with Written Opinion of the International Searching Authority (English Translations) for PCT Application No. PCT/CN2017/080906; The International Bureau of WIPO; Geneva, Switzerland, dated Oct. 30, 2018.

Australian Examination Report for Australian Patent Application No. 2017255549; Australian Patent Office; Sydney, Australia; dated Apr. 5, 2019.

Chinese first Office action and Search Report for Chinese Patent Application No. 201610272984.8; China National Intellectual Property; Beijing, China; dated Apr. 2, 2019.

Chinese second Office action for Chinese Patent Application No. 201610272984.8; China National Intellectual Property; Beijing, China; dated Dec. 3, 2019.

Chinese third Office action for Chinese Patent Application No. 201610272984.8; China National Intellectual Property; Beijing, China; dated Aug. 4, 2020.

European Extended Search Report for European Patent Application No. 17788679.3; European Patent Office; Munich, Germany; dated Dec. 12, 2019.

Japanese first Office action for Japanese Patent Application No. 2018-556911; Japanese Patent Office;Tokyo, Japan; dated Sep. 2019.

Japanese second Office action, Notice of Reason for Refusal, for Japanese Patent Application No. 2018-556911; Japanese Patent Office;Tokyo, Japan; dated Aug. 2020.

Korean first Office action for Korean Patent Application No. 10-2018-7033249; Korean Intellectual Property Office; Daejeon Metropolitan City, South Korea; dated Jul. 1, 2020.

Turkish first Examination Report for Turkish Patent Application No. 2018/15810; Turkish Patent and Trademark Office; Ankara, Turkey; dated Jun. 30, 2021.

* cited by examiner

TOOL BIT FOR AN ULTRASONIC OSTEOTOME

CROSS REFERENCE TO RELATED APPLICATIONS

This is a Continuation application of International Application Serial No. PCT/CN2017/080906, filed on Apr. 18, 2017, which claims the benefit of Chinese Application No. 201610272984.8, filed on Apr. 28, 2016, the disclosures of which are hereby incorporated by reference.

BACKGROUND

The present disclosure relates to the field of medical instruments and devices, in particular to a scalpel, and more particularly to a tool bit for an ultrasonic osteotome.

In modern society, with the development of medical technology, orthopedic surgery shows a trend of diversity. Accordingly, when performing surgery, it is necessary to use different tool bits for a scalpel to perform cutting, grinding, scraping, clamping and other operations on an affected part in a patient according to different orthopedic conditions of disease.

In view of the special construction of bone structure, along with the continuously development of ultrasound technology in recent years, an ultrasonic osteotome has gradually become a main tool for modern orthopedic surgery. An ultrasonic osteotome employs high-intensity focused ultrasound technique that converts electrical energy to mechanical energy through a transducer, and evaporates water in the contacted tissue cells and breaks protein hydrogen bonds through high-frequency ultrasound concussion, so as to completely destroy bone tissues to be cut in surgery. Since the high-intensity focused ultrasound only has a destructive effect on bone tissues of a specific hardness and has a characteristic of cutting hard things rather than soft things, it is particularly suitable for spinal surgery in which the peripheral structure is a bone structure and the middle structure is a soft tissue as a spinal cord. Surgery with an ultrasonic osteotome can effectively prevent the occurrence of medical accidents during the operation such as an injury to the spinal cord due to excessive force, thereby improving the safety of the operation.

In the prior art, when a doctor performs an osteotomy with an ultrasonic osteotome, the surgeon relies mainly on the surgical experience to control the cutting depth and force. In the process of cutting, different types of tool bits need to be replaced to achieve different cutting effects, thereby greatly reducing the surgical efficiency, increasing the workload of the medical worker, prolonging the operation time, and the medical staff is more prone to fatigue. At the same time, constant replacement of the tool bit will interrupt the doctor's surgical operation, break the continuity of the operation, and undermine the operation feeling during the operation. As is well known, surgery operation is a manual process for manipulating a device. People with hands-on experience understand that when doing precision operations, it should be done at one go without interruption. In the process of operation, the operator and the device will find the best state of each other, achieving perfect coordination. If this process is interrupted frequently due to replacements of tool bits, the operator will need to be adapted to the new tool bit repeatedly so as to find perfect feeling again, which will greatly decrease the operation efficiency and increase the risk of surgery as well as setting higher demands on the surgeon, thus increasing the workload of doctors and decreasing the rate of success in surgeries.

BRIEF SUMMARY

In view of the existing problems, the present disclosure provides a tool bit for an ultrasonic osteotome to address the above drawbacks.

As a solution of the present disclosure to address the problems in the prior art, a tool bit for an ultrasonic osteotome is provided, comprising a cutting portion at a front end of the tool bit for an ultrasonic osteotome, a connecting portion at a rear end of the tool bit for an ultrasonic osteotome and connected to the cutting portion. The cutting portion has a grinding part for grinding and a blade for cutting at a front end of the cutting portion, and the grinding part and the blade are integrally formed.

Preferably, the cross sections of the grinding part and the blade assume a shape of an umbrella, the grinding part is located at a position of an umbrella canopy, and the blade is located at a position of the umbrella handle.

Preferably, an outer surface of the grinding part is divided into a plurality of bumps by a plurality of crisscrossed grooves, wherein a plurality of grooves running in an axial direction extends toward a rear end of the cutting portion and terminates in a middle portion of the cutting portion so as to form longitudinal grooves for guiding liquid.

Preferably, the blade comprises a transition part connected to the grinding part and a cutting edge connected to the transition part and located on a side opposite to the grinding part, the cutting edge is divided into separated tooth-shaped structures by a plurality of circular arcs arranged at intervals, the tooth-shaped structures having sharp edges.

Preferably, the blade comprises a transition part connected to the grinding part and a cutting edge connected to the transition part and located on a side opposite to the grinding part, and the cutting edge is provided with a plurality of side cutting edges on two sides thereof respectively, and the side cutting edges are parallel to each other and perpendicular to an extreme edge of the cutting edge and extend toward the grinding part.

Preferably, the cutting edge extends upwardly and wraps around a front end of the grinding part.

Preferably, the transition part smoothly joins the grinding part and the blade, and the transition part extends radially outwardly to form a stop surface for defining a cutting depth of the blade.

Preferably, a front end of the connecting portion forms frustum structure, a small end of which is connected with the cutting portion, and a large end thereof extends toward a tail end of the tool bit to form a cylinder structure, and a plurality of flat faces for clamping are formed along an outer surface of the cylinder structure on a side thereof near the large end of the frustum structure.

Preferably, the tool bit for an ultrasonic osteotome is of a hollow structure, and an internal thread for connecting a handle of the ultrasonic osteotome is provided at a tail end of the connecting portion.

Compared with the prior art, embodiments of the present invention have the following advantages: the tool bit for an ultrasonic osteotome has an integral structure of the grinding part and the blade, and the medical workers can use the tool bit for an ultrasonic osteotome for multiple uses during an operation with no need to replace the tool bit frequently, resulting in the operation time being reduced, the efficiency of surgery being greatly improved, as well as the risk of surgery and the sufferings of a patient being decreased. The tool bit for an ultrasonic osteotome of the disclosure is exquisite and compact, and can accurately control the cutting amount and cutting shape of a bone, thus reducing the amount of bone loss during an operation, and accelerating the recovery of a patient. According to the ultrasonic characteristics of the ultrasonic osteotome, it is also possible to perform hemostasis and coagulation on the wound, so as to reduce the amount of surgical bleeding and further alleviate sufferings of a patient. At the same time, the integration of two different types of tool bits can also lower production costs together with human power and material resources saving. The tool bit for an ultrasonic osteotome of the disclosure can be operated conveniently and comfortably with high safety.

Figure 1:
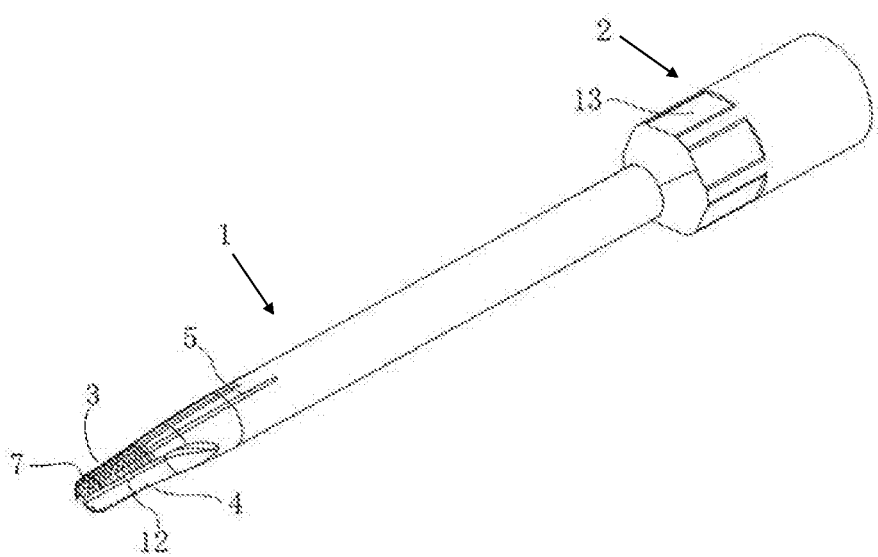
FIG. 1 is a schematic perspective view of a tool bit for an ultrasonic osteotome according to a first embodiment of the present invention.

LIST OF REFERENCE NUMERALS 1-cutting portion, 2-connecting portion, 3-grinding part, 4-blade, 5-longitudinal groove, 6-transition part, 7-bump, 8-cutting edge, 9-curved portion, 10-straight portion, 11-arc, 12-stop surface, 13-clamping flat face, 14-side cutting edge, 15-internal thread.

DETAILED DESCRIPTION

Exemplary embodiments of the present disclosure will be described hereinafter clearly and completely with reference to the attached drawings. Apparently, the embodiments described herein are only portions of embodiments of the disclosure, rather than all embodiments of the disclosure. It is intended that all other embodiments obtained by those skilled in the art according to the disclosed embodiments without inventive labor are within the scope of the present invention.

In the description of the present disclosure, it is to be noted that the terms of "center", "upper", "lower", "left", "right", "vertical", "horizontal", "internal", "external" and the like simply indicate orientational or positional relationship based on the accompanying drawings and are used only for the purpose of facilitating and simplifying the description of the invention, rather than specifying or implying that any device or elements indicated must have a certain orientation, constitute with a certain orientation, or operate in a certain orientation. Therefore, these terms will not be interpreted as limiting the present invention. Further, the terms of "first", "second" and "third" are only used for describing purpose, rather than being interpreted as specifying or implying relative importance.

In the description of the present disclosure, it is to be noted that, unless otherwise specified or defined clearly, the term of "attach, "connect to", "connect with", "couple" and the like should be interpreted broadly. For example, they may refer to fixed connection, or detachable connection, or integral connection; they may refer to mechanical connection, or electrical connection; they may refer to direct connection, or indirect connection through an intermediate agent, or internal communication between two components. For those skilled in the art, the specific meaning of these terms in the present disclosure may be understood in combination with specific situations or contexts.

FIG. 1 is a schematic perspective view of a tool bit for an ultrasonic osteotome according to a first embodiment of the present invention. As shown in FIG. 1, the tool bit for an ultrasonic osteotome of the first embodiment comprises a cutting portion 1 at a front end of the tool bit for an ultrasonic osteotome and a connecting portion 2 at a rear end of the tool bit for an ultrasonic osteotome and connected to the cutting portion 1. A front end of cutting portion 1 has a grinding part 3 for grinding and a blade 4 for cutting, and grinding part 3 and blade 4 are formed into an integral structure.

When performing an operation using the tool bit for an ultrasonic osteotome of the present embodiment, firstly, a surgeon uses a sharp cutting edge 8 of blade 4 of the tool bit for an ultrasonic osteotome to quickly cut a body tissue, then he or she rotates the handle so that grinding part 3 faces downward and uses the grinding characteristics of grinding part 3 to expand a surgical wound. By repeating these steps, it is possible to realize quick cutting on a body tissue. During the process, the tool bit for an ultrasonic osteotome does not need to be replaced frequently, thus reducing the operation time, greatly improving the efficiency of surgeries, reducing risks of surgery and sufferings of a patient. The tool bit for an ultrasonic osteotome of the disclosure is exquisite and compact, and can accurately control the cutting amount and cutting shape of a bone, thus reducing the amount of bone loss during the operation, and accelerating the recovery of a patient. According to the ultrasonic characteristics of the ultrasonic osteotome, it is also possible to perform hemostasis and coagulation on the wound, thus reducing the amount of surgical bleeding, and further alleviating sufferings of a patient. At the same time, the integration of two different types of tool bits can also lower production costs and save human power and material resources. The tool bit for an ultrasonic osteotome of the disclosure can be operated conveniently and comfortably with high safety.

Figure 2:
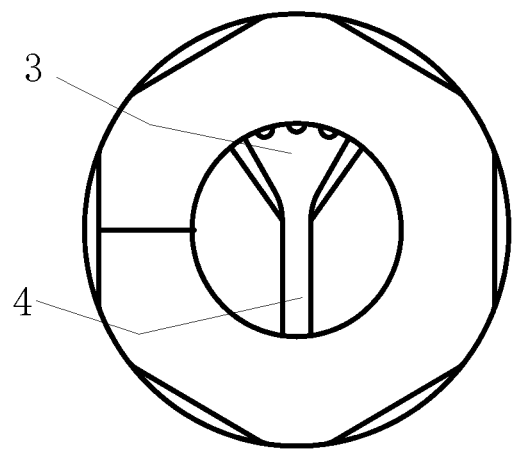
FIG. 2 is a schematic right side view of the tool bit for an ultrasonic osteotome according to the first embodiment of the present invention.

FIG. 2 is a right side view of the tool bit for an ultrasonic osteotome according to the first embodiment of the present invention. As shown in FIG. 2, a cross section of grinding part 3 and blade 4 may be in the shape of an umbrella, grinding part 3 is located at a position of an umbrella canopy, and blade 4 is located at a position corresponding to an umbrella handle. Different sizes of grinding parts 3 can be designed according to different surgical requirements. For example, the shape of the umbrella canopy of grinding part 3 may be semi-circular or semi-elliptical, or a slightly pointed shape. In short, any suitable shape can be chosen for grinding part 3 if only it can enable grinding part 3 to contact a body tissue in a large-area and perform a grinding operation on a body tissue. Preferably, an opening angle of a fan shape of grinding part 3 is between 10° and 180° in order to perform a grinding operation on a bone tissue effectively.

Figure 3:
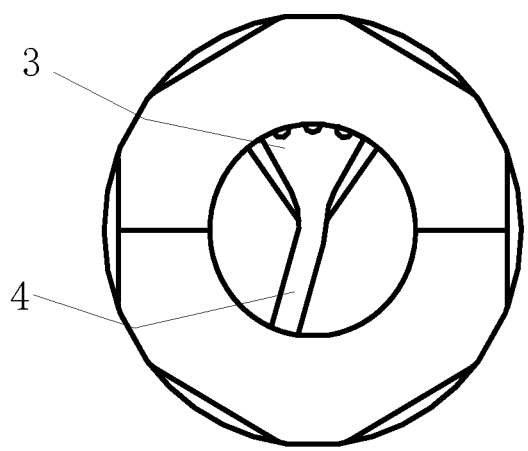
FIG. 3 is a schematic right side view of the tool bit for an ultrasonic osteotome according to a second embodiment of the present invention.

FIG. 3 is a schematic right side view of a tool bit for an ultrasonic osteotome according to a second embodiment of the present invention. Compared with the first embodiment of the present invention, in the second embodiment, the central lines of grinding part 3 and blade 4 are at an angle so as to be adapted to a bone structure of different shape.

Figure 4A:
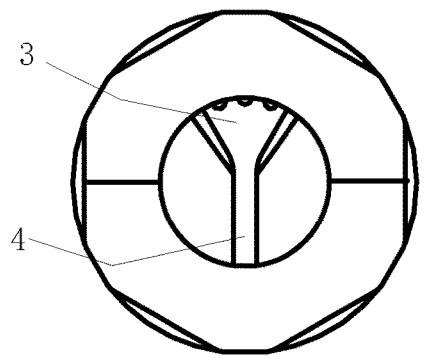
FIGS. 4A and 4B are schematic right side views showing a tool bit for an ultrasonic osteotome according to a third embodiment of the present invention.
Figure 4B:
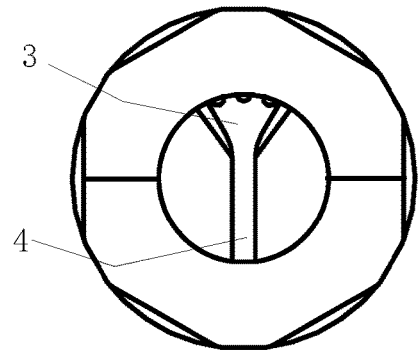

FIGS. 4A-4B are schematic right side views of a tool bit for an ultrasonic osteotome according to a third embodiment of the present invention. Compared with the first embodiment, in the third embodiment of the present invention, the height ratio of grinding part 3 to blade 4 may be varied, for example, the heights of grinding part 3 and blade 4 may be the same or different. In the case where the size of the tool bit is constant, when the height of blade 4 is small as shown in FIG. 4A, the cutting depth of blade 4 can be precisely controlled to achieve an accurate operation; and when the height of blade 4 is large as shown in FIG. 4B, the cutting amount can be increased and the operation efficiency can be improved.

Figure 5:
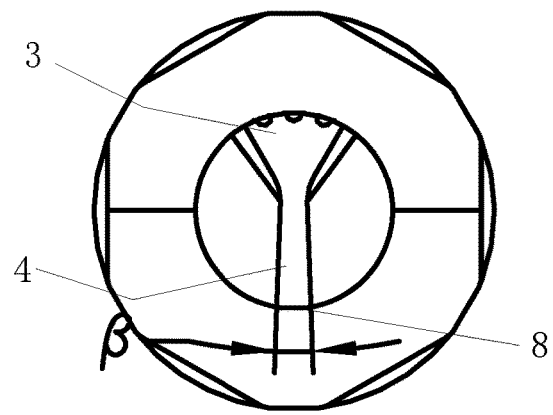
FIG. 5 is a schematic right side view of a tool bit for an ultrasonic osteotome according to a fourth embodiment of the present invention.

FIG. 5 is a schematic right side view of the tool bit for an ultrasonic osteotome according to a fourth embodiment of the present invention. Compared with the first and third embodiments of the present invention, in the fourth embodiment of the present invention, there is an angle β formed by two side surfaces of blade 4, and the angle of β may be ranged from −15° to +15°, with the angle opening toward cutting edge 8.

In the above embodiments, an outer surface of the grinding part 3 may be divided into a plurality of bumps 7 by a plurality of crisscrossed grooves. A plurality of the grooves running in an axial direction extends toward the rear end of the cutting portion 1 and terminates in the middle portion of the cutting portion 1, so as to form longitudinal grooves 5 for guiding liquid. Longitudinal grooves 5 mainly have two functions: first, the longitudinal grooves 5 can serve as liquid guiding grooves to introduce surgical operation liquids into cutting portion 1 more smoothly, thereby cleaning and cooling body tissues; second, longitudinal grooves 5 serve as partition grooves, together with lateral grooves cutting in a circumferential direction, divide the outer surface of grinding part 3 to form a plurality of bumps 7, thereby realizing the grinding function of grinding part 3. Preferably, longitudinal grooves 5 terminate in the middle portion of cutting portion 1 and form smooth transition with the outer surface of cutting portion 1 so as to facilitate introduction of surgical operating fluids into the longitudinal grooves 5. The shape of the plurality of bumps 7 may be a cube, a polyhedron with a pointed end facing up, etc., and sizes and shapes of bumps are determined by shapes of intersecting grooves forming bumps 7. Which shape of bumps 7 should be used can be designed based on different requirements of surgical operations. Generally, the cube-shaped plane bumps 7 are more advantageous for large area grinding operations; the pointed bumps 7 are more advantageous for smashing bone tissues.

Figure 6:
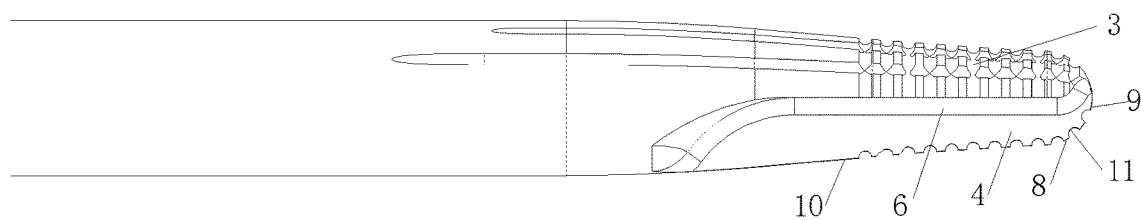
FIG. 6 is a schematic front view showing a tool bit for an ultrasonic osteotome according to a fifth embodiment of the present invention.

FIG. 6 is a schematic front view showing a tool bit for an ultrasonic osteotome according to a fifth embodiment of the present invention. In the fifth embodiment of the present invention, as shown in FIG. 6, a blade 4 includes a transition part 6 connected to grinding part 3, and a cutting edge 8 connected to said transition part 6 on a side opposite to grinding part 3. Cutting edge 8 is divided into separated tooth structures by a plurality of circular arcs 11 arranged at a certain interval, and the edges of the tooth structures are sharp. On the one hand, the cutting edge 8 with the sharp tooth structures can concentrate ultrasonic energy, increase energy conversion efficiency, and perform an operation more quickly and conveniently. On the other hand, the cutting edge 8 itself is divided into a plurality of small blades arranged in a straight line by a plurality of circular arcs 11, so that for a single cutting on a body tissue, there will be multiple times of scratching and cutting process, which will enable surgery to perform an labor-saving and high efficiency operation.

As shown in FIG. 6, a portion of grinding part 3 located at a front end of cutting portion 1 may have a round structure, which is a typical shape of a tool bit for a scalpel, rendering a smooth and small outer surface of grinding part 3, resulting in an easy fine-grinding operation.

As shown in FIG. 6, a blade 4 includes a transition part 6 which is connected to grinding part 3 and a cutting edge 8 which is connected to transition part 6 and is located on a side opposite to said grinding part 3. A front end of cutting edge 8 may be a curved portion 9, a rear end of cutting edge 8 may be a straight portion 10, and there is a smooth transition between curved portion 9 and straight portion 10. This smooth transition structure is advantageous for an operator to use the ultrasonic osteotome to cut into the bone tissue conveniently. Grinding part 3 that cooperates with the curved cutting edge 8 may have any shape such as a square shape, a round shape, and a pointed shape.

Figure 7:
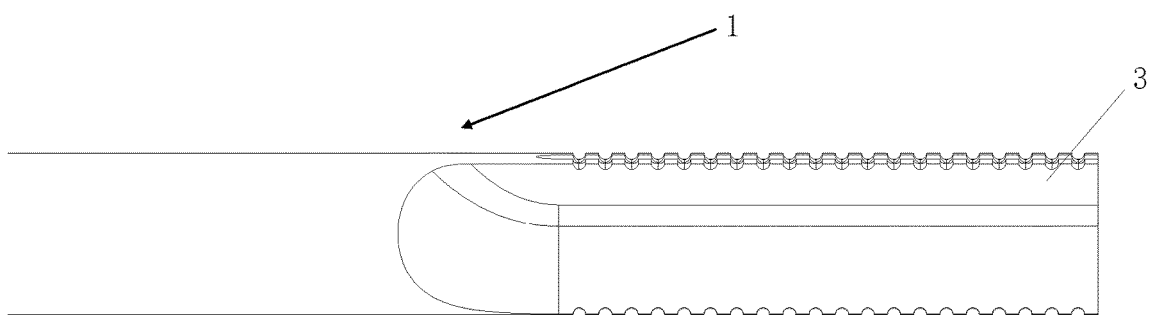
FIG. 7 is a schematic front view showing a tool bit for an ultrasonic osteotome according to a sixth embodiment of the present invention.

FIG. 7 is a schematic front view of a tool bit for an ultrasonic osteotome according to a sixth embodiment of the present invention. In contrast to the fifth embodiment of the present invention, in the sixth embodiment of the present invention, a portion of grinding part 3 located at the front end of cutting portion 1 has a square structure. The square-shaped end portion of cutting portion 1 has a sharp right-angled edge, which is advantageous for concentrating ultrasonic energy. Therefore, for some kind of body tissues requiring high energy for grinding operation, the square-shaped grinding part 3 is more advantageous than a round structure.

Figure 8:
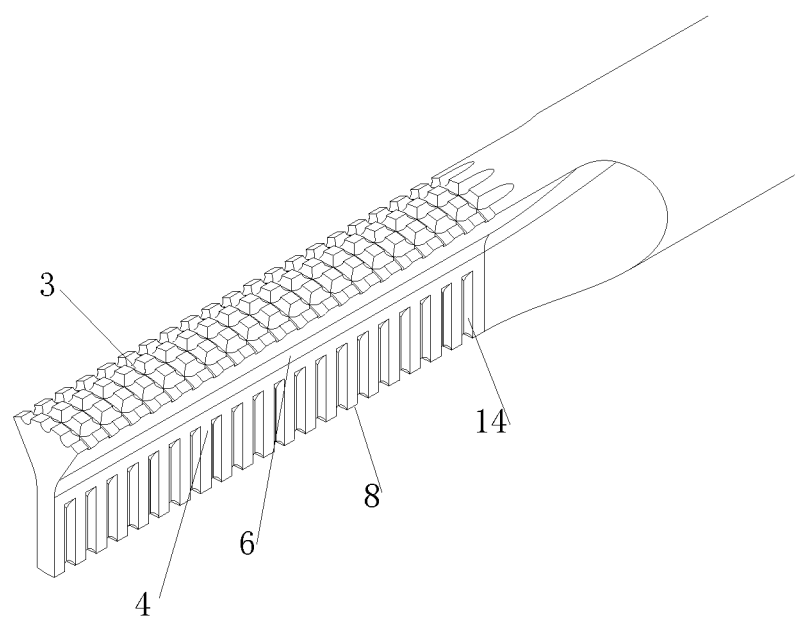
FIG. 8 is a schematic perspective view showing a cutting portion of a tool bit for an ultrasonic osteotome according to a seventh embodiment of the present invention.

FIG. 8 is a perspective view showing a tool bit for an ultrasonic osteotome according to a seventh embodiment of the present invention. As shown in FIG. 8, in the seventh embodiment of the present invention, a blade 4 of the tool bit for an ultrasonic osteotome includes a transition part 6 which is connected to grinding part 3 and a cutting edge 8 which is connected to transition part 6 and is located on a side opposite to said grinding part 3. A plurality of parallel side cutting edges 14 perpendicular to the pointed edge of cutting edge 8 and extending toward the grinding part 3 are provided on two sides of the cutting edge 8 respectively. The side cutting edges 14 have sharp edges, which is more advantageous for cutting a body tissue.

Specifically, side cutting edges 14 can be formed by forming grooves on the side of blade 4. Grooves may be formed only on one side of blade 4, or grooves may be formed on both sides of blade 4. Some of the grooves may be penetrated in a thickness direction of blade 4 so that a part of the blade may have a comb-like structure, or all the grooves may be penetrated in a thickness direction of blade 4 so that the blade may have a comb-like structure as a whole. The lengths and depths of respective grooves may be varied arbitrarily to be different from each other. In a tool bit for an ultrasonic osteotome of the present embodiment, side cutting edges 14 are formed on side surfaces of the blade 4, which can avoid slippage between blade 4 and a bone during an operation, so as to further improve the positioning accuracy and cutting speed, thus improving the surgical efficiency and accuracy, shortening the operation time, and reducing the pain of a patient. In the case where grooves are dense, that is, the number of side cutting edges 14 is large, the cutting speed is faster and the positioning effect is better. When deeper grooves are formed in blade 4, the cutting efficiency is much higher in an operation for a hard bone having a higher degree of calcification. On the other hand, for shallow grooves, the overall strength of the tool bit can be ensured to prevent the tool bit from breaking during an operation. Therefore, by appropriately setting depths of various grooves on blade 4, in an operation for hard bones having a high degree of calcification, the cutting speed during the operation and the life of the blade can be ensured, and the surgical efficiency and the safety can be well balanced.

Further, said grooves may be inclined toward a front end of a tool bit so as to form an angle less than 90 degrees with the cutting edge 8, i.e., a bottom edge of blade 4. In this way, by tilting grooves toward a front end of a tool bit, the flow direction of rinsing liquid can be controlled during the operation, so that the effect of flushing and cooling during the operation can be further improved.

Figure 9:
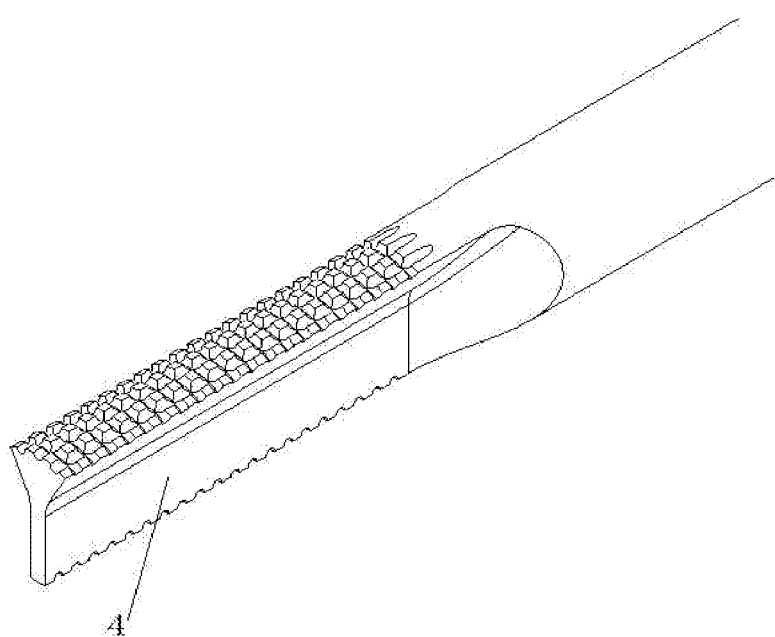
FIG. 9 is a schematic perspective view showing a cutting portion of a tool bit for an ultrasonic osteotome according to a eighth embodiment of the present invention.

FIG. 9 is a schematic perspective view of a tool bit for an ultrasonic osteotome according to an eighth embodiment of the present invention. As shown in FIG. 9, in the eighth embodiment of the present invention, a blade 4 has a rectangular parallelepiped structure as a whole, and its front end extends vertically upward and intersects a grinding part 3. Blade 4 of this shape is easy to be machined, and its tip is sharp, which is more advantageous for concentrating ultrasonic energy and accelerating the surgical process.

Further, in FIG. 6, blade 4 may also extend upward and curve around a front end of grinding part 3 and form a cutting edge 8 at the front end of grinding part 3. The shape of cutting edge 8 may be various shapes such as a semi-circular arc, a pointed circular arc, and a straight edge, as long as the tool bit can effectively cutting a body tissue when it is placed perpendicularly to the body tissue. A structure that cutting edge 8 wraps around a front end of grinding part 3 enables a surgeon using an ultrasonic osteotome erectly to cut a narrow gap in a body tissue, resulting in expanded applications of the ultrasonic osteotome, facilitated in achieving a precise surgical cutting, as well as improved surgical efficiency. At the same time, the surgical trauma is decreased and cure rate is improved.

Preferably, in each of the above embodiments, transition part 6 connects grinding part 3 and blade 4 in a smooth manner, and transition part 6 extends radially outwardly to form a stop surface 12 for defining the cutting depth of the blade 4, as shown in FIG. 1. When a surgeon operates an ultrasonic osteotome to cut a body tissue, when the cutting depth reaches the height of blade 4, stop surface 12 will abut against the outside of an incision, which will limit further penetration of blade 4, so as to effectively prevent accident caused by improper operation of the surgeon due to excessive cutting of a body tissue with too much strength. Stop surface 12 is formed by that the transition part 6 extends radially outwardly, and may be a flat surface, a concave surface, a curved surface, or any other suitable shape, as long as it can properly limit the cutting depth of blade 4. A flat surface is preferred, which is convenient for machining and cleaning. Transition part 6 is connected with blade 4 in a smooth manner with a fillet radius preferably ranging from 0.5 mm to 10 mm.

In each of the above embodiments, a front end portion of connecting portion 2 of the tool bit for an ultrasonic osteotome has a frustum structure, and a small end thereof is connected to cutting portion 1, and a large end thereof extends toward the tail end of the tool bit to form a cylinder structure, as shown in FIG. 1. A plurality of flat faces 13 for being clamp are formed along the outer surface of the cylinder structure on a side of the cylinder structure near the large end of the frustum structure. The flat faces 13 are designed primarily to facilitate clamping of the tool bit with a tool. The flat faces may be arranged in an even number and symmetrically distributed in pairs. The number of the flat faces may also be an odd number, and when installing, a special fixture may be sleeved on the outside the flat faces to perform rotating operation.

Figure 10:
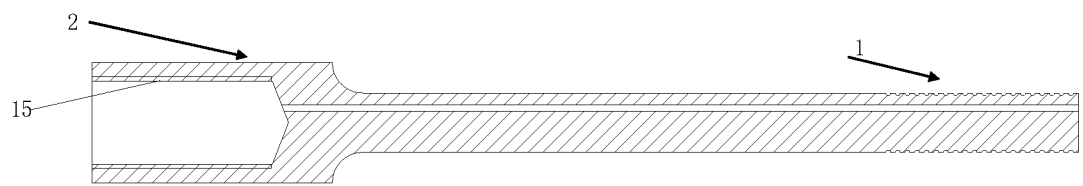
FIG. 10 is a schematic cross-sectional view showing the hollow structure of the tool bit for an ultrasonic osteotome of the present invention.

FIG. 10 is a schematic cross-sectional view showing a hollow structure of a tool bit for an ultrasonic osteotome according to an embodiment of the present invention. As shown in FIG. 10, the tool bit for an ultrasonic osteotome has a hollow structure, and an internal thread 15 for connecting a handle of the ultrasonic osteotome is provided at a tail end of the connecting portion. On the one hand, the design of the hollow structure can save materials, making the tool bit lighter and more flexible; on the other hand, it can also improve heat dissipation performance of the tool bit, and at the same time, medical liquids can flow through it, further improving heat dissipation performance and lubrication effect.

Compared with the prior art, embodiments of the present invention have the following advantages: the tool bit for an ultrasonic osteotome is of an integral structure formed by the grinding part 3 and the blade 4. During an operation, a medical person can use the tool bit for an ultrasonic osteotome for multiple uses with no need to replace the tool bit frequently, thus reducing the operation time, greatly improving the efficiency of surgery, reducing the risk of surgery and the sufferings of a patient. According to the ultrasonic characteristics of the ultrasonic osteotome, it is also possible to perform hemostasis and coagulation on the wound, reducing the amount of surgical bleeding, and further alleviating sufferings of a patient. At the same time, the integration of two different types of tool bits can also reduce production costs and save human power and material resources. The tool bit for an ultrasonic osteotome of the disclosure can be operated conveniently and comfortably with high safety.

It should be noted that the above embodiments are only used to describe the concept of the present invention, rather than limiting the present invention. Although detailed descriptions of the invention are made with reference to the above embodiments, it would be appreciated by those skilled in the art that various changes or modifications to the above embodiments may be made or equivalent substitutions to portion of or all features in those embodiments may be made. Such changes, modifications or substitutions will not make the spirit of the relevant solutions depart from the scope of the present invention, which is defined in the claims and their equivalents.

What is claimed is:

1. A tool bit for an ultrasonic osteotome, comprising:
a cutting portion located at a front end of the tool bit for an ultrasonic osteotome, and a connecting portion located at a rear end of the tool bit for an ultrasonic osteotome and connected to the cutting portion, wherein the cutting portion and the connecting portion extend along a longitudinal axis of the tool bit;
wherein the cutting portion has a grinding part for grinding and a blade for cutting, at a front end thereof, and the grinding part and the blade are integrally formed;
wherein a cross section of the cutting portion taken transverse to the longitudinal axis of the tool bit assumes a shape of an umbrella, with an outer grinding surface of the grinding part extending about an arc of a canopy of the umbrella shape, and with the blade extending radially from the grinding part along a handle of the umbrella shape such that a cutting edge of the blade is located on an end opposite the outer grinding surface.

2. The tool bit for an ultrasonic osteotome according to claim 1, wherein the outer grinding surface of the grinding part is divided into a plurality of bumps by a plurality of crisscrossed grooves, among which a plurality of the grooves running in a longitudinal direction extends toward a rear end of the cutting portion and terminates in a middle portion of the cutting portion to form longitudinal grooves for guiding liquid.

3. The tool bit for an ultrasonic osteotome according to claim 1, wherein the blade comprises a transition part connected to the grinding part and the cutting edge Which is connected to the transition part and located on the end opposite to the outer grinding surface, the cutting edge is divided into separated tooth-shaped structures by a plurality of circular arcs arranged at intervals, the tooth-shaped structures having sharp edges.

4. The tool bit for an ultrasonic osteotome according to claim 3, wherein the cutting edge extends upwardly and wraps around a front end of the grinding part.

5. The tool bit for an ultrasonic osteotome according to claim 3, wherein the transition part smoothly joins the grinding part and the blade, and the transition part extends radially outwardly to form a stop surface for defining a cutting depth of the blade.

6. The tool bit for an ultrasonic osteotome according to claim 1, wherein the blade comprises a transition part connected to the grinding part and the cutting edge connected to the transition part and located on the end opposite to the outer grinding surface, and the cutting edge is provided with a plurality of side cutting edges on two sides thereof respectively, and the side cutting edges are parallel to each other and perpendicular to an extreme edge of the cutting edge and extend toward the grinding part.

7. The tool bit for an ultrasonic osteotome according to claim 6, wherein the transition part smoothly joins the grinding part and the blade, and the transition part extends radially outwardly to form a stop surface for defining a cutting depth of the blade.

8. The tool bit for an ultrasonic osteotome according to claim 1, wherein a front end of the connecting portion forms a frustum structure, a small end of the frustum structure is connected with the cutting portion, and a large end of the frustum structure extends toward a tail end of said tool bit to form a cylinder structure, and a plurality of flat faces for clamping are formed along an outer surface of the cylinder structure on a side thereof near the large end of the frustum structure.

9. The tool bit for an ultrasonic osteotome according to claim 1, wherein the tool bit for an ultrasonic osteotome is of a hollow structure, and an internal thread for connecting a handle of an ultrasonic osteotome is provided at a tail end of the connecting portion.

\* \* \* \* \*

UNITED STATES PATENT AND TRADEMARK OFFICE
CERTIFICATE OF CORRECTION

PATENT NO. : 11,207,084 B2  
APPLICATION NO. : 16/170687  
DATED : December 28, 2021  
INVENTOR(S) : Feng et al.

It is certified that error appears in the above-identified patent and that said Letters Patent is hereby corrected as shown below:

In the Claims

Column 9, Line 32, Claim 3:
"cutting edge Which is" should read --cutting edge which is--.

Signed and Sealed this
Nineteenth Day of April, 2022

Katherine Kelly Vidal
*Director of the United States Patent and Trademark Office*